United States Patent
Putzer

(10) Patent No.: US 6,482,194 B1
(45) Date of Patent: Nov. 19, 2002

(54) POCKET DESIGN FOR ABSORBENT ARTICLE

(75) Inventor: Melissa C. Putzer, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/471,561

(22) Filed: Dec. 23, 1999

(51) Int. Cl.[7] .............................................. A61F 13/15
(52) U.S. Cl. ............................ 604/385.19; 604/385.24; 604/385.27
(58) Field of Search .................... 604/385.16, 385.19, 604/385.22, 385.24, 385.27, 385.28

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,561,446 A | 2/1971 | Jones, Sr. | 128/287 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,890,973 A | 6/1975 | Davis et al. | 128/286 |
| 4,340,563 A | 7/1982 | Appel et al. | 264/518 |
| 4,560,380 A | 12/1985 | Tharel | 604/385 R |
| 4,950,262 A | 8/1990 | Takagi | 604/385.1 |
| 5,057,368 A | 10/1991 | Largman et al. | 428/307 |
| 5,062,840 A | 11/1991 | Holt et al. | 604/385.1 |
| 5,069,970 A | 12/1991 | Largman et al. | 428/373 |
| 5,277,976 A | 1/1994 | Hogle et al. | 428/397 |
| 5,462,541 A | 10/1995 | Bruemmer et al. | 604/391 |
| 5,466,410 A | 11/1995 | Hills | 264/172.11 |
| 5,527,303 A | 6/1996 | Milby, Jr. et al. | 604/385.1 |
| 5,601,543 A * | 2/1997 | Dreier et al. | 604/85.1 |
| 5,795,348 A * | 8/1998 | Roe et al. | 604/85.1 |
| 5,817,086 A * | 10/1998 | Kling | 604/385.2 |
| 5,830,203 A * | 11/1998 | Suzuki et al. | 604/385.2 |
| 5,833,677 A | 11/1998 | Sauer | 604/369 |
| 5,843,056 A | 12/1998 | Good et al. | 604/367 |
| 5,853,403 A * | 12/1998 | Tanzer et al. | 604/385.1 |
| 5,895,382 A | 4/1999 | Popp et al. | 604/385.2 |
| 5,904,674 A * | 5/1999 | Bonjour | 604/385.2 |
| 6,152,908 A * | 11/2000 | Widlund et al. | 604/385.19 |
| 6,168,583 B1 * | 1/2001 | Tanji et al. | 604/385.14 |
| 6,186,996 B1 * | 2/2001 | Martin | 604/385.19 |
| 6,254,583 B1 * | 7/2001 | Coates | 604/385.14 |

FOREIGN PATENT DOCUMENTS

| | | | |
|---|---|---|---|
| EP | 226 789 | 7/1987 | A41B/13/02 |
| WO | 98/17217 | 4/1998 | A61F/13/15 |
| WO | 98/27907 | 7/1998 | A61F/13/15 |
| WO | 98/53779 | 12/1998 | A61F/13/15 |

* cited by examiner

Primary Examiner—Glenn K. Dawson
Assistant Examiner—Michael G. Bogart
(74) Attorney, Agent, or Firm—Pauley Petersen Kinne & Erickson

(57) ABSTRACT

An absorbent article having a material formed as a single piece having two enlarged end portions and a narrowed portion intermediate the enlarged end portions and arranged for wearing by an individual. The material includes a fluid permeable topsheet, a fluid impermeable backsheet and an absorbent layer disposed between the fluid permeable topsheet and the fluid impermeable backsheet. Integral pleats extending along opposed side of a longitudinal centerline of the material between the enlarged end portions are provided for expanding at least the absorbent layer and the fluid impermeable backsheet away from the skin of the individual for collection of fecal matter.

10 Claims, 3 Drawing Sheets

POCKET DESIGN FOR ABSORBENT ARTICLE

BACKGROUND OF THE INVENTION

1. Field of the Invention

This invention relates to diapers or other absorbent articles, such as training pants, incontinence garments and the like and, more particularly, to a diaper or absorbent article having means for isolation and containment of waste material from the body.

2. Description of Prior Art

A typical disposable diaper or other absorbent article of the type contemplated by this disclosure comprises a fluid-permeable topsheet, a fluid-impermeable backsheet, an absorbent assembly between the topsheet and the backsheet, and a means for fastening the diaper or article to the wearer. Materials used in the manufacture of such disposable articles include polymeric films and nonwovens, including spunbond fibers or webs, meltblown fibers or webs and bonded carded webs. Although current diapers or other absorbent articles have been generally accepted by the public, there is still a need for improvement in certain areas, particularly in the area of isolating and containing waste material away from the skin of the wearer. And, although current diapers or absorbent articles have been generally satisfactory in preventing leakage of urine outside of the diaper or absorbent article, the waste material contained therein too often is in contact with the skin of the wearer. If this contact between waste material and the skin is prolonged over a period of time, it can cause undesirable effects such as skin dermatitis, skin hydration, or messy clean-ups.

One solution to this problem is the integration of a pocket into the diaper or absorbent article for collection of solid fecal material. Such a pocket, disposed toward the back of the diaper or absorbent article prevents leaks, especially of feces. The pocket is formed by a multi-layer material comprising a fluid permeable topsheet, a fluid impermeable backsheet and an absorbent layer disposed between the topsheet and the backsheet. Extra material in the topsheet and the backsheet create a pocket or depression for feces to collect in away from the skin of the wearer. U.S. Pat. No. 5,462,541 teaches a pocket-like diaper or absorbent article comprising a backsheet, a topsheet having an opening, an absorbent assembly or layer between the backsheet and the topsheet, and an elevating device below the topsheet that spaces the topsheet above the absorbent layer, thereby forming a pocket-like shape for isolating and containing waste material.

Having extra material in the topsheet and backsheet to provide room for containment of solids the entire length of the product has several drawbacks including extra material costs and material bunching where a solids void volume is not needed, such as the front of the product where liquid exudates are excreted.

SUMMARY OF THE INVENTION

It is one object of this invention to provide a method for producing a diaper or absorbent article having a pocket, which method utilizes no more material than the amount of material required for producing a diaper or other absorbent article having full length pleats or a conventional pocket design.

This and other objects are addressed by an absorbent article comprising a material formed as a single piece having two enlarged end portions and a narrowed portion intermediate the enlarged end portions and arranged for wearing by an individual. The material comprises a fluid permeable topsheet, a fluid impermeable backsheet and an absorbent layer disposed between the fluid permeable topsheet and the fluid impermeable backsheet. Expansion means for expanding at least the absorbent layer and the fluid impermeable backsheet away from the skin of the individual for collection of fecal matter are provided, which expansion means comprise at least one integral pleat extending along opposed sides of the longitudinal centerline of the material between the two enlarged end portions.

In accordance with one preferred embodiment of this invention, the expansion means comprises a back pocket, which, due to the integral pleats is able to move away from the body of the wearer. One benefit of the execution of the pocket using an integral pleat is a reduction in the amount of waste material in that additional material from the leg cut out of the diaper, that is material which would otherwise be discarded, is used to form the pleat in the buttock region. In addition, a flush fit can be maintained at the front and back waist because the extra material is not full length. The extra material in the leg cut out, depending upon its size and shape can deliver void volume, additional coverage and expansion in the machine direction, cross machine direction and Z direction of the product.

A method for producing a diaper or other absorbent article having a pocket for isolation and containment of solid fecal matter away from the body of the wearer in accordance with one embodiment of this invention comprises forming a substantially rectangular multi-layer material comprising a fluid permeable topsheet, a fluid impermeable backsheet, and an absorbent layer disposed between the fluid permeable topsheet and the fluid impermeable backsheet, removing a portion of the multi-layer material from opposed longitudinal edges of the material resulting in formation of two enlarged end portions and a narrowed intermediate portion, whereby the narrowed intermediate portion of the multi-layer material comprises a bulge along a portion of each opposed longitudinal edge. The bulge is pulled laterally toward the longitudinal centerline of the multi-layer material resulting in alignment of the bulges with a remaining portion of the opposed edges of the narrowed intermediate portions and formation of a depression or pocket toward the back of the diaper for collection of fecal matter. In accordance with one embodiment of this invention, a second topsheet which forms an opening toward the back of the product may also be incorporated for additional separation.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Definitions

Figure 1:
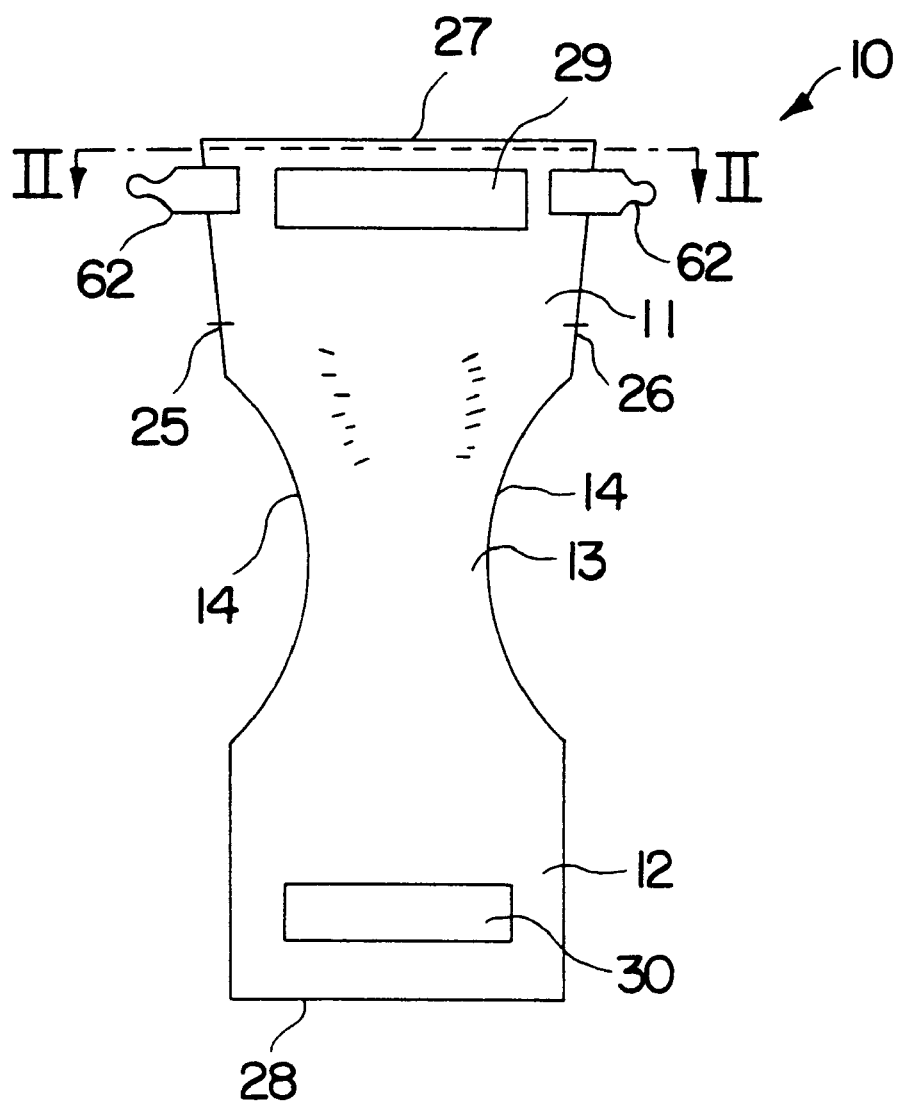
FIG. 1 is a top plan view of a disposable diaper in accordance with one embodiment of this invention.

As used herein, the term "comprising" is inclusive or open-ended and does not exclude additional unrecited elements, compositional components, or method steps.

As used herein, the term "nonwoven" or "nonwoven web" means a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

The terms "elastic" and "elastomeric" are used interchangeably to mean a material that is generally capable of recovering its shape after deformation when the deforming force is removed.

As used herein, the term "machine direction" or "MD" means the length of a fabric in the direction in which it is produced. The term "cross machine direction" or "CD" means the width of fabric, that is a direction generally perpendicular to the MD. The term "Z direction" refers to a direction generally perpendicular to the machine direction and the cross machine direction.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "microfibers" refers to small diameter fibers having an average diameter not greater than about 100 microns, for example, having an average diameter of from about 0.5 microns to about 50 microns, or more particularly, having an average diameter of from about 2 microns to about 40 microns. Another frequently used expression of fiber diameter is denier, which is defined as grams per 9000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the results by 0.89 g/cc and multiplying by 0.00707. Thus, a 15 micron polypropylene fiber has a denier of about 1.42. Outside the United States, the unit of measurement is more commonly the "tex", which is defined as the grams per kilometer of fiber. Tex may be calculated as denier/9.

The absorbent article of the present invention can be utilized as a baby diaper, adult incontinence garment, and the like. For purposes of the present discussion, the absorbent article will be described in terms of a baby diaper, but it is to be understood that the features and principles of the present invention may also apply to other types of absorbent articles.

Figure 2:
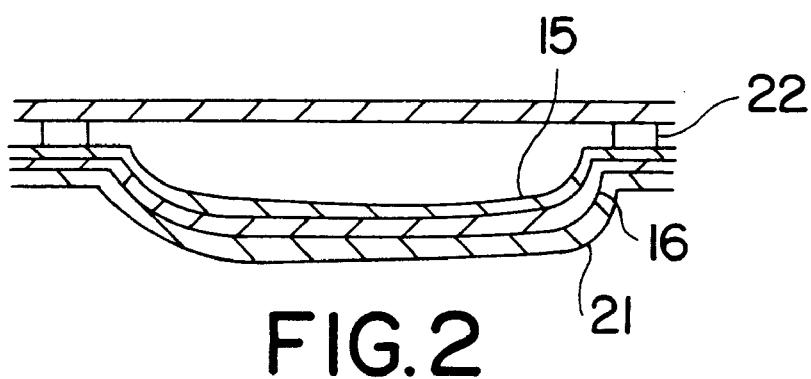
FIG. 2 is a schematic diagram of a cross-sectional view of the disposable diaper of FIG. 1 taken along the line II—II.
Figures 4A, 4B, 4C:
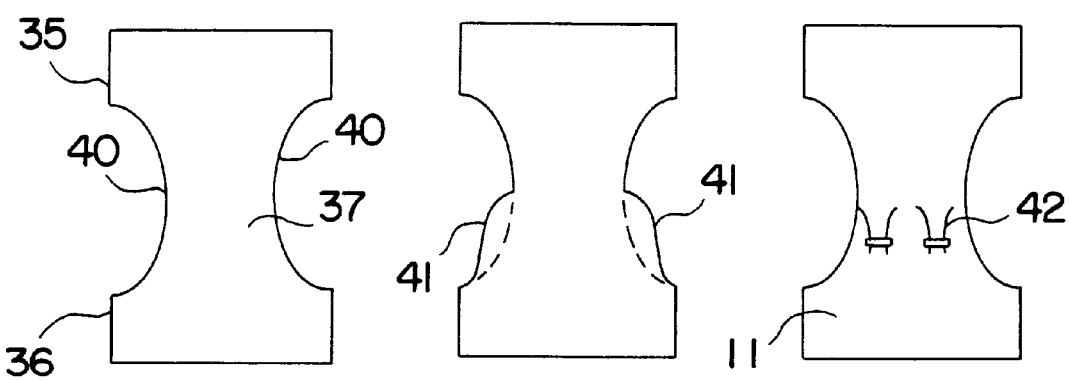
FIGS. 4A, 4B and 4C show a top plan view of a standard diaper/leg cut out, an integrated pleat leg cut out, and an integrated pleat leg cut out pulled in to line up with a standard leg cut out.

The invention disclosed herein in accordance with one embodiment is a disposable diaper comprising a back pocket for reception, isolation and containment of solid fecal matter away from the body of the wearer. Referring to FIG. 1, diaper 10 in accordance with one embodiment of this invention, shown in a flat, uncontracted state, comprises a material formed as a single piece having two enlarged end portions 11, 12 and a narrowed portion 13 intermediate the enlarged end portions 11, 12. For purposes of this description, enlarged end portion 12 corresponds to the front waist section of the diaper and enlarged end portion 11 corresponds to the back or rear waist section of the diaper. The front and rear waist sections include the general portions of the diaper which are constructed to extend substantially over the wearer's front and rear abdominal regions, respectively, during use. The narrowed portion of the diaper includes the general portion of the article which is constructed to extend through the wearer's crotch region between the legs. The opposed longitudinal side edges 25, 26 define leg cut outs 14 which preferably are curved or contoured to more closely fit the legs of the wearer and which include a bulge area 41 as shown in FIG. 4B. The opposed end edges 27, 28 define a waist opening for the diaper and typically are straight, although they may be curvilinear. The material as shown in FIG. 2 further comprises a fluid permeable topsheet or body side liner 15 and a fluid impermeable backsheet 21 having an absorbent layer 16 disposed therebetween. Marginal sections of backsheet 21 may extend past the terminal edges of the absorbent layer 16. The topsheet 15 is generally coterminous with the backsheet 21 but may optionally cover an area which is larger or smaller than backsheet 21. To provide better fit and to aid in reducing leakage, the longitudinal side edges 25, 26 and the end edges 27, 28 may be elasticized with suitable elastic members such as leg elastic members 55 shown in FIG. 5B and waist elastic members 29, 30. For example, the leg elastic members 55 may include single or multiple strands of elastic or elastomeric composites which are constructed to operably gather and shirr the longitudinal side edges 25, 26 of the diaper to provide elasticized leg bands which can fit closely around the legs of the wearer. Similarly, the waist elastic members 29, 30 can be employed to elasticize the end edges 27, 28 thereby providing elasticized waistbands.

Elastic members 29, 30, 55 are secured to the material in an elastically contracted condition whereby in a normal under strain configuration, the elastic members effectively contract against the material.

The diaper as shown in FIG. 1 may further include a pair of fasteners or ears 62 which are used to secure the diaper around the waist of the wearer. Suitable fasteners include hook-and-loop type fasteners, adhesive type fasteners, buttons, pins, snaps and the like.

FIGS. 4B and 4C are diagrammatic representations of a diaper in accordance with this invention showing the integral pleat which is formed in such a way so as to produce a smooth flush fit at both the front and back of the diaper as shown in FIG. 2 while still providing expansion capability for formation of the pocket. The amount of material required for this execution is no greater than the amount of material employed in the production of a conventional diaper having no pocket.

FIG. 4A is a plan view of a conventional diaper having enlarged end portions 35, 36 and narrowed intermediate portion 37. Narrowed intermediate portion 37 is narrowed as a result of the removal of material along the opposed longitudinal side edges for formation of leg cut outs 40. It is apparent that material removed for the purpose of forming leg cut outs 40 is material which is wasted. FIGS. 4B and 4C are representative of a method for producing an integral pleat, thereby increasing the void volume of the pocket, in accordance with the embodiment shown in FIG. 2, whereby the amount of waste material removed for formation of leg cut outs is reduced and no additional material for pleating is required. This is achieved by leaving a bulge 41 in the leg cut out area and then pulling the bulge laterally toward the interior of the diaper until alignment with the remaining portion of what corresponds to a standard leg cut out is achieved to create an integral pleat or pucker 42 in the buttock region of the diaper. The extra material of the bulge 41 in the leg cut out area, depending upon its size and shape can provide void volume, additional coverage and expansion in the machine direction, the cross machine direction and the Z-direction of the product.

Figure 5A:
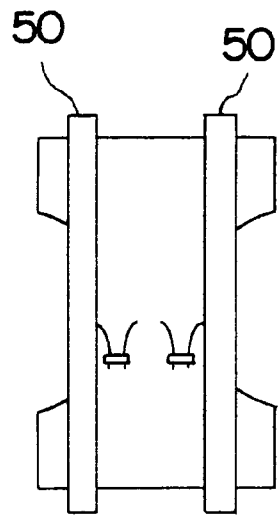
FIGS. 5A and 5B show a top plan view of a cuff or flap attached to the edge of the leg cut out.
Figure 5B:
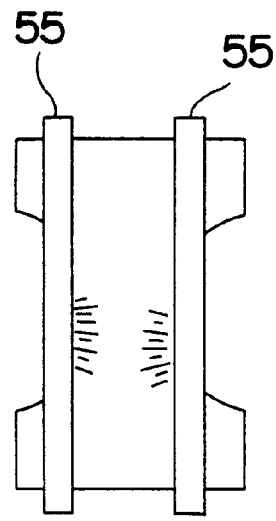

After pinching of the material to form integral pleats or puckers 42, a flap or combination flap and leg elastic 50, 55 as shown in FIGS. 5A and 5B is attached in a straight manner to the edge of the pulled in leg cut out profile. The manner in which the bulges 41 in the leg cut outs 40 change determines how the pleat will expand in the machine direction, the cross machine direction and the Z-direction of the product. The extent of the bulge 41 is generally limited by the overall width of the product. The backsheet and lower liner could also be puckered in to provide swelling volume for the absorbent or for a swellable spacer between the backsheet and the topsheet.

Figure 3:
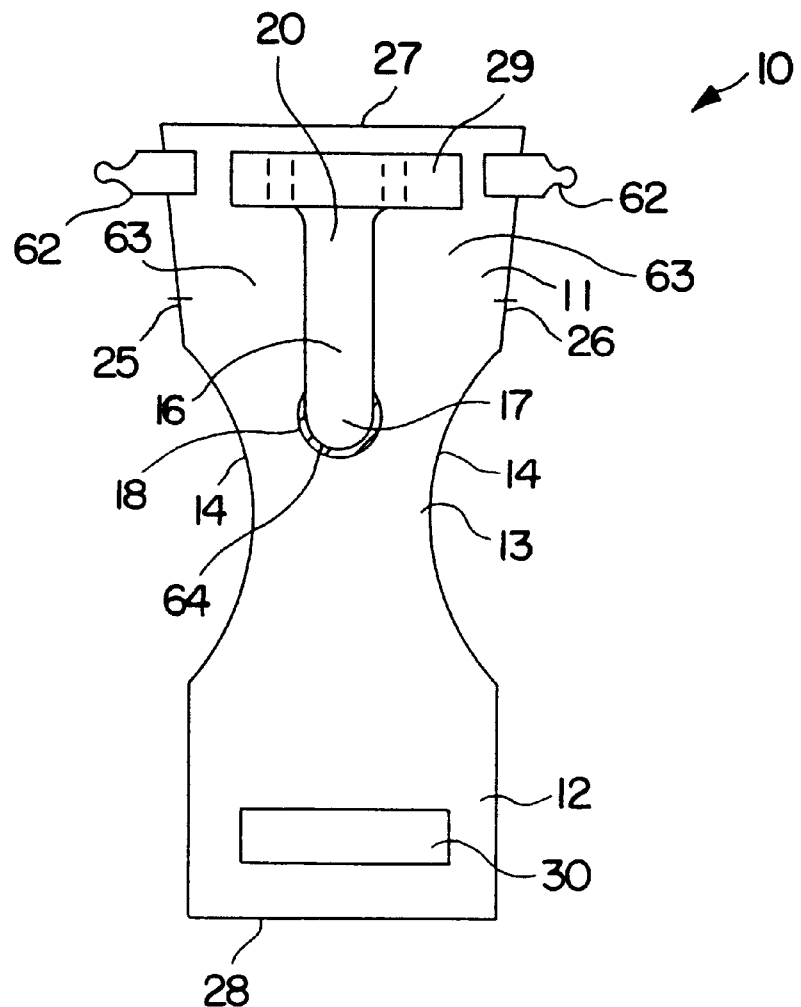
FIG. 3 is a top plan view of a disposable diaper in accordance with one embodiment of this invention.

In accordance with one embodiment of this invention as shown in FIG. 3, topsheet 15 forms opening 17 whereby fecal matter is permitted to pass through topsheet 15 on to absorbent layer 16 and, due to the presence of pocket means for elevating at least a portion of topsheet 15 away from absorbent layer 16, a pocket 20 is formed enabling the solid fecal matter to be isolated from the skin of the wearer while being contained within the diaper. Topsheet 15 has a generally U- or horseshoe-shape in which the elongated portions form containment flaps 63. The horseshoe shape may be manufactured by tucking or folding a cut portion of topsheet 15 upon itself starting at its longitudinal centerline and between rear end edge 27 to a point toward the front section of the article identified as apex 64. Prior to cutting and folding topsheet 15 upon itself to form containment flaps 63, an elastic member 18 is applied in a stretched condition in the crotch region adjacent to and outboard of, relative to the longitudinal centerline, its respective longitudinal fold line. Elastic members 18 are then covered by topsheet 15 in the cutting and folding step. Due to elastic member 18, elevation of at least a portion of topsheet 15 away from absorbent layer 16 is enabled. Due to attachment of elastic member 18 to topsheet 15 in a stretched condition, upon relaxing, topsheet 15 will curl in an upward direction toward the wearer's body and away from absorbent layer 16.

To produce a disposable absorbent article having a pocket in accordance with one embodiment of this invention, a substantially rectangular multi-layer material comprising a fluid permeable topsheet, a fluid impermeable backsheet, and an absorbent layer disposed between the fluid permeable topsheet and the fluid impermeable backsheet is formed and a portion of the material from opposed longitudinal edges is removed, as shown in FIG. 4A, forming two enlarged end portions 35, 36 and a narrowed intermediate portion 37. The narrowed intermediate portion 37 forms leg cut outs 40 along opposed edges of the narrowed intermediate portion 37.

The narrowed intermediate portion 37 of the backsheet 21 comprises a bulge 41 along a portion of each leg cut out 40 toward the rear section of the absorbent article as shown in FIG. 4B, and the backsheet 21 and absorbent layer 16 are gathered toward an interior of the narrowed intermediate portion 37, resulting in alignment of the bulges 41 with the remaining portion of the leg cut outs 40 as shown in FIG. 4C. The gathered portions 42 of the backsheet 21 and the absorbent layer 16 are used for formation of the pocket 20.

In accordance with one embodiment of this invention, an opening 17 in the topsheet 15 suitable for passage of fecal matter to said absorbent layer 16 is formed and the topsheet 15 is connected to the backsheet 21 such that the backsheet 21 is longitudinally pleated between the enlarged end portions, enabling the absorbent layer 16 and the backsheet 21 to expand away from the topsheet 15. Backsheet 21 and absorbent layer 16 are attached to topsheet 15 as shown in FIG. 2 by point bonds 22. It will be apparent to those skilled in the art that other connection means may be employed, such as, for example adhesives.

As can be seen from the previous description, the "extra" material utilized for formation of the pocket is obtained by leaving attached a portion of the leg cut out material which would normally be discarded and "pulling on" this additional material until it is aligned flush with the remaining portion of the leg cut out. In order to produce a leg cut out with a "bulge" requires that the water cutter or die normally used to produce a standard leg cut out, such as that shown in FIG. 4A, would have to be altered so as to produce this non-standard leg cut out.

Figure 6A:
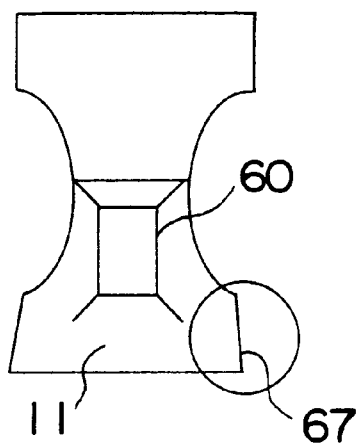
FIGS. 6A and 6B are diagrams showing a "tent" method for forming a pocket with an integrated pleat.

In accordance with one embodiment of the method of this invention, the use of a special water cutter or die to form the bulges 41 within the leg cuts 40 is avoided by pulling an interior portion of the backsheet 21 and absorbent layer 16 proximate the diaper back 11 and the narrowed intermediate portion 13 out of the initial plane of the material so as to form a tent-like structure 60 as shown in FIG. 6A and then cutting a standard leg cut out pattern. The "tent" 60 is the inverse of what the pocket 20 will be when flap 50 or leg elastic materials 55 are attached in a straight fashion to the diaper when the tent or pocket is held in place.

Figure 6B:
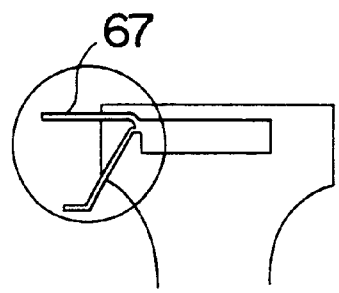
Figure 7:
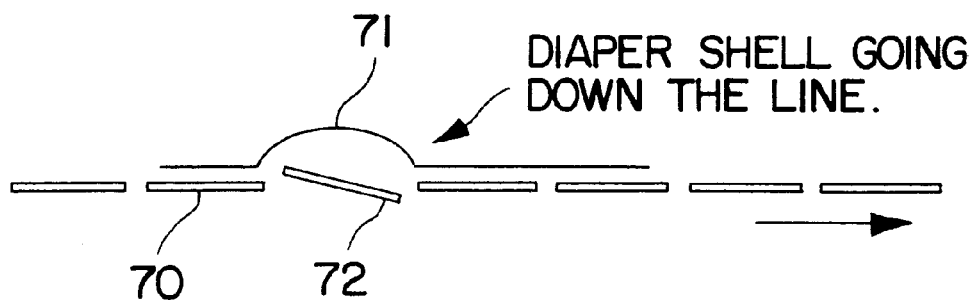
FIG. 7 is a cross-sectional diagram of a belt line having a segmented section for formation of an inverse tent for formation of the pocket when the diaper or absorbent article is in use.

A further benefit of the "tent" method, is that the tent may also pull the edge or ear 67 toward the interior of the diaper or shorten the end of the diaper back, thereby providing the normally straight ear with a slightly angled appearance when the extra pocket material is anchored between the flaps or leg elastics as shown in FIG. 6B. This angling provides a better fitting angled ear shape. Depending upon the size of the "tent" structure 60, the leg cut out 40 can also be changed or shaped to a more curved flowing leg opening profile. This line may not be possible at higher manufacturing speeds with some leg cutting equipment because of the need to quickly return inward to make the next leg cut out. The tenting or raising of the backsheet to pull the materials in for a more severe cut could be done with a segment track 70, 72 in a process belt carrying the product shells 71 as shown in FIG. 7. The segments 72 in the track could be raised and lowered by gears or intermittently phased air. If the flap or leg elastic material is attached in a straight fashion while the extra material is held inward, a pocket will be formed. If the material is held up prior to cutting the leg cut out but lowered to be flat before the flap or leg elastic material is attached, a pocket will not be formed, but the angled ear or a more severe leg cut out profile will be gained.

The segments 72 to be raised during the manufacturing process can be any size or shape. A figure eight pocket configuration or one with ins and outs could be used to form multiple individual depressions. The depth of the pocket can be drastic or gradual with a ramped or angled edge to the raised segments. The segments may be tear drop shaped to fit the contours of the buttocks or legs. The leg curve and degree of angling of the ears may also be varied limitlessly depending upon the height, width and length and profile of the segments raised during forming. The height of the block segments may also be varied such that it will curve the waist section of the diaper. A downward smile shaped curve may be formed at the front waist which would be helpful in avoiding the umbilical cord of newborns while the back of the diaper would be higher for better coverage and protection against back waist leaks. This would be formed with a straight cut off because the tent shaping would provide the bias for curving.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. An absorbent article comprising:

a material formed as a single piece having two enlarged end portions and a narrowed portion intermediate said enlarged end portions and arranged for wearing by an individual, said material comprising a fluid permeable topsheet, a fluid impermeable backsheet and an absorbent layer disposed between said fluid permeable topsheet and said fluid impermeable backsheet; and at least one gathered portion formed by the backsheet and the absorbent layer gathered toward an interior of the narrowed portion, the at least one gathered portion forming a pocket for collection of fecal matter, wherein a portion of opposed side edges of said material is pulled laterally inward toward an interior of said material extending between said enlarged end portions, and one of a flap and a flap and leg elastic composite is attached in a straight fashion to said opposed side edges and extends between opposed edges of said enlarged end portions.

2. An absorbent article in accordance with claim 1, wherein said topsheet forms an opening for passage of said fecal matter to said absorbent layer.

3. An absorbent article in accordance with claim 2, wherein at least a portion of said topsheet peripheral to said opening is elasticized.

4. An absorbent article in accordance with claim 2, wherein said topsheet is U-shaped with elongated portions which constitute containment flaps.

5. An absorbent article in accordance with claim 1, wherein one of said enlarged end portions corresponds to a rear waist section of said absorbent article and a fastening ear is disposed on opposed sides of said rear waist section, said fastening ears being angled outward with respect to a longitudinal centerline of said absorbent article.

6. A diaper comprising:

an outer cover, an absorbent layer and a body-side liner; and at least one gathered portion formed by the outer cover and the absorbent layer gathered toward an interior of a narrowed portion of the diaper, the at least one gathered portion forming a pocket for collection of fecal matter, wherein a portion of opposed side edges of said at least one of said body-side liner and said outer cover is pulled laterally inward toward an interior of said diaper, and one of a flap and a flap and leg elastic composite is attached in a straight fashion to said opposed side edges and extends between said front waist section and said rear waist section.

7. A diaper in accordance with claim 6, wherein a fastening ear is disposed on opposed sides of said rear waist section, said fastening ears being angled out ward with respect to a longitudinal centerline of said diaper.

8. A diaper in accordance with claim 6, further comprising a fluid permeable topsheet connected to at least one of said body-side liner and said outer cover on a body facing side of said diaper, said topsheet forming an opening for passage of said fecal matter to said body-side liner.

9. A diaper in accordance with claim 8, wherein at least a portion of a periphery of said opening is elasticized.

10. A diaper in accordance with claim 8, wherein said topsheet is U-shaped with elongated portions which constitute containment flaps.

* * * * *